United States Patent [19]

Rogers

[11] Patent Number: 4,918,311
[45] Date of Patent: Apr. 17, 1990

[54] SET POINT CONTROL CIRCUIT FOR AN INFRARED GAS ANALYZER

[75] Inventor: Raymond E. Rogers, Oakland, Calif.

[73] Assignee: Andros Analyzers Incorporated, Berkeley, Calif.

[21] Appl. No.: 181,929

[22] Filed: Apr. 15, 1988

[51] Int. Cl.⁴ ............................................. G01N 21/61
[52] U.S. Cl. .................................. 250/343; 250/252.1; 250/352
[58] Field of Search ................ 250/252.1 A, 343, 352; 356/437

[56] References Cited

U.S. PATENT DOCUMENTS

| 4,233,513 | 11/1980 | Elder et al. | 250/343 |
| 4,398,091 | 8/1983 | Passaro | 250/343 |
| 4,687,934 | 8/1987 | Passaro et al. | 250/343 |

FOREIGN PATENT DOCUMENTS

222993  5/1987  European Pat. Off. ...... 250/252.1 A

*Primary Examiner*—Carolyn E. Fields
*Attorney, Agent, or Firm*—McCubbrey, Bartels, Meyer & Ward

[57] ABSTRACT

An arrangement for ensuring the stability of the set point for a gas analyzer is disclosed. The set point control circuit utilizes an amplifier which is alternately switched between a reference voltage and a sensor signal to provide a signal to a processor representing the reference signal and the sensor signal. The processor compares the two signals and adjusts the heater associated with the sensor to provide a stable set point for the gas analyzer. The arrangement eliminates the need for precision resistors within the set point control circuit and therefore significantly reduces the cost of the circuitry.

28 Claims, 5 Drawing Sheets

SET POINT CONTROL CIRCUIT FOR AN INFRARED GAS ANALYZER

FIELD OF THE INVENTION

This invention relates to infrared gas analyzers and, more particularly, to a method and apparatus for providing a stable set point in gas analyzer control systems.

BACKGROUND OF THE INVENTION

Non-dispersive infrared gas analyzers typically utilize an infrared source to produce and direct infrared energy through an unknown gas mixture contained in a sample cell. The energy passing through the sample cell at certain predetermined wavelengths is detected and electrical signals are produced representative thereof. The predetermined wavelengths are selected to correspond with the characteristic frequency absorption of a gas or gasses of interest. The electrical signals are processed to produce an output indicating the concentration of one or more of the gases in the gas mixture in the sample cell.

One such analyzer is described in Passaro et al., U.S. Pat. No. 4,346,296. In this disclosure, an infrared source emits infrared radiation at relatively constant intensity over a relatively broad spectrum. The infrared radiation from the source is interrupted periodically by a chopper wheel. After passing through the sample cell, the chopped infrared radiation is detected by respective detectors. In each case the radiation is filtered by a narrow passband filter so that each detector is effectively sensitive only to the radiation of a particular narrow band of frequencies corresponding to a respective absorption frequency characteristic of the respective gas.

The respective detection signals are thus systematically related to the relative concentration of the respective gases. Because of the chopper wheel, these signals are AC signals at the chopper wheel frequency. The signals are then amplified, detected and filtered to produce corresponding DC signals.

Each filtered signal is applied to one input of a so-called span amplifier. A span amplifier typically comprises a summing amplifier which receives an offset reference input signal and a controllable feedback input signal. The offset reference signal offsets a zero point of the analyzer, and the feedback signal controls the span or the magnitude of the input signal required for providing a full-scale output.

The feedback signal is controlled by the span amplifier to balance out the offset signal to allow for the zero point to be determined. What is meant by "zero point" in this application is that the span amplifier in the absence of absorption of the incident infrared radiation should produce a zero output. As described in the aforesaid U.S. Pat. No. 4,346,296, the zero point of the span amplifier is adjusted by introducing a so-called zero gas in to the sample cell and adjusting the gain control on the feedback signal input to provide a zero meter reading. The zero gas is a gas, such as nitrogen, which is substantially non-absorptive of infrared energy, at least at the frequencies passed by the respective filters.

When a predetermined calibrating gas is introduced into the sample cell, the gain of the feedback signal is adjusted to some predetermined calibrated value. Then, when the gas to be analyzed is introduced, the output meter properly records or indicates the relative concentration of the respective constituent gases.

U.S. Pat. No. 4,687,934, entitled "Infrared Gas Analyzer With Automatic Zero Adjustment" in the names of Robert E. Passaro, Raymond E. Rogers and J. Craig Griffith, describes an automatic zero apparatus for an infrared gas analyzer. This apparatus comprises a comparator with a gain control which automatically controls the signal level of the detector signal from the span amplifier to reduce the output signal substantially to zero when the non-absorbent gas is within the sample cell. The aforementioned patent utilized a programmable microprocessor which provides a zeroing operation which is repeated after a predetermined period of time or upon a temperature drift of the gas analyzer above a predetermined level. The above-mentioned elements eliminate the necessity of having an operator adjust the system manually to a proper zero condition.

The above-mentioned patents disclose infrared gas analyzers that automatically provide a zero point over a predetermined period of time and upon a temperature drift above a predetermined level. It is also known, however, that gas analyzers of the above-mentioned type also exhibit set point instability due to variations in the temperature of the source, as well as variations in the temperature of the detectors. U.S. Pat. No. 4,398,091, issued in the name of Passaro, teaches a gas analyzer which compensates for these variations. Accordingly, oftentimes heaters are placed in the appropriate places within the analyzers and are then monitored to maintain the temperature of the gas analyzer at a fixed temperature to eliminate many of the drift corrections that are necessary when the ambient temperature changes. In so doing, the gas analyzer is more stable and therefore can more accurately measure the concentration levels of the various gases.

Generally, the monitoring of these elements is performed by a control circuit in conjunction with the processor providing a "set point" for the gas analyzer. What is meant by the set point in the context of the present application is the calibration point to which the device is set at a known gas and gas concentration, from which the gas measurements can be taken. To ensure that the readings of the gas analyzer are accurate, certain parameters such as temperature of the source and temperature of the heaters should be stable before the gas is measured. Accordingly, these parameters are monitored and adjusted to provide for the "set point" of the gas analyzer.

To control the set point, the measured temperature signals of the gas analyzer are provided to a set point circuit. These signals are compared to a reference signal. If the temperature signals do not correspond to the reference signal, then a processor within the gas analyzer will adjust the heaters' temperature until the appropriate output signal is obtained. Consequently, it is important that the set point be stable to ensure that the subsequent measurements made by the gas analyzer are accurate.

Typically, a differential amplifier circuit has been utilized to provide the stable set point in a gas analyzer by comparing the output signal of the temperature sensors associated with the heaters to some reference signal. If a predetermined signal is not present on the output of the amplifier, the processor then adjusts the temperature of the heater until the proper output voltage is present.

Although a differential amplifier works effectively as a set point control circuit within a gas analyzer, it requires a plurality of precision resistors for proper operation. Precision resistors are required because their values interact to provide the output voltage of the set point control circuit. As is well known, when a common input signal is provided to the two inputs of a differential amplifier, the differential mode output signal is zero. As a practical matter, however, it is also known that if both input terminals are at exactly the same potential, but the potential of both is varied together, some output voltage variation will occur. This output variation is called a common mode error signal. Accordingly, a common mode error signal represents an inaccuracy if the input signals are the same. This error can be minimized by ensuring that the input resistances are carefully matched. Therefore, precision resistors are utilized to minimize the common mode error.

It is known that precision resistors are expensive and can significantly increase the cost of a device. More particularly, it is very important in a gas analyzer to keep the overall costs as low as possible. It has been found that the use of a differential amplifier circuit in this context increases the need for the precision resistors and therefore undesirably increases the cost of the gas analyzer used therewith.

Accordingly, any system, device or apparatus that decreases the cost of the gas analyzer represents a significant advance over the art. More particularly, any arrangement which would limit the number of precision resistors necessary in a set point control circuit utilized in a gas analyzer and still maintain the stability thereof would represent a significant improvement over previously known circuits.

Broadly, it is an object of the present invention to provide an infrared gas analyzer with an improved set point control circuit.

It is a further object of the present invention to provide a circuit for providing a stable output signal for a given input signal over a predetermined temperature range and time interval.

It is also an object of the present invention to provide a gas analyzer that has a stable set point control circuit that is less expensive than previously known set point control circuitry utilized therewith.

SUMMARY OF THE INVENTION

The set point control circuit for a gas analyzer comprises a reference signal generator and a sensor for generating a sense signal, the sense signal being dependent on a parameter of the gas analyzer. The circuit also includes an amplifier which is adapted to be selectively coupled to the reference signal generator and the sensor. The amplifier provides a signal representative of the reference signal when coupled thereto and provides a signal representative of the sensor when coupled thereto.

A processor is utilized in the circuit for selectively switching the amplifier between the reference signal generator and the sensor. The reference and sensor signals are compared within the processor. The processor then adjusts the parameter associated with that sensor signal until it corresponds to the reference signal.

In one embodiment, the sensed parameter is the temperature of heaters within the gas analyzer. Accordingly, a sensor associated with each heater provides a signal which is representative of that temperature. A set point circuit provides an output signal representative of the reference voltage to the processor when connected thereto. The set point circuit provides an output signal to the processor representative of the sensor voltage when connected thereto. If the signals are not equal, then the processor will adjust the associated heater temperature until both the sensor and the reference signal provide the same output to the processor.

Through this arrangement, a set point control circuit is provided that ensures the accuracy and stability of the gas analyzer. No precision components are required in the set point control circuit because the comparison of signals is accomplished by the processor. Hence, the cost of the set point control circuit is less than those utilized in previous gas analyzers.

BRIEF DESCRIPTION OF THE DRAWINGS

The advantages of the present invention will become more apparent from the following detailed description and drawings in which.

DETAILED DESCRIPTION

Figure 1:
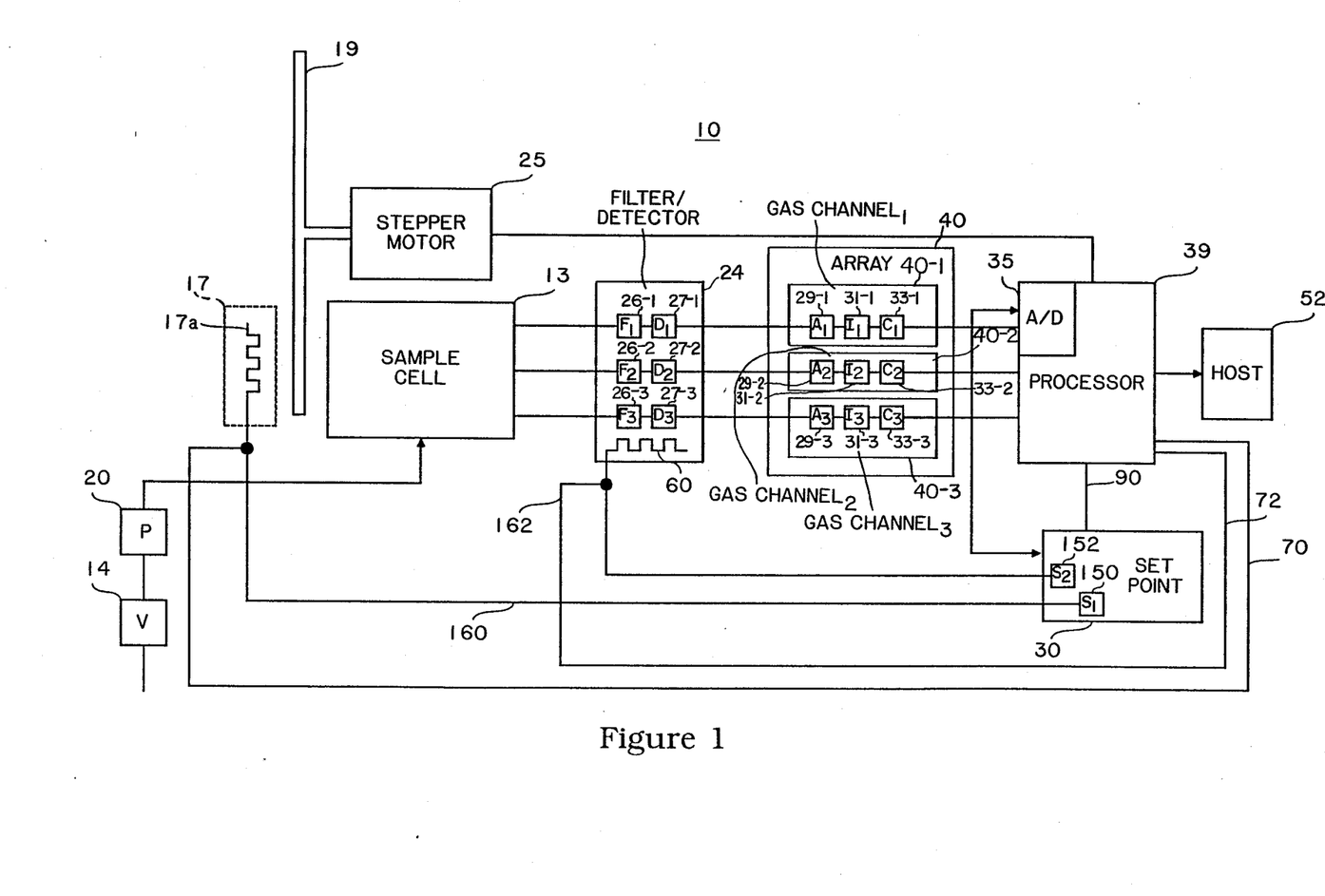
FIG. 1 is a simplified block diagram of a gas analyzer.

Shown in FIG. 1 is a diagram of the infrared gas analyzer 10 of the present invention. The gas analyzer 10 includes a sample cell 13 that receives a gas mixture to be detected. An infrared source 17 directs infrared energy through the sample cell 13. The infrared path is periodically interrupted by a chopper wheel 19. The chopper wheel 19 under control of processor 39 is actuated by stepper motor 25. The source 17 has a heater element 17a which is under the control of processor 39 in response to the set point circuit 30. A detector/filter assembly 24 receives the infrared energy exiting sample cell 13. Set point circuit 30 is thermally coupled to the heater 60 of the filter/detector 24. The set point circuit 30 provides the initial measurement parameters for the gas analyzer 10.

The set point circuit 30 receives signals from sensors 150 ($S_1$) and 152 ($S_2$) that are representative of temperatures of the filter/detector assembly 24 and the source 17, respectively, and in turn provides those signals to the analog to digital (A/D) converter 35. The A/D converter 35 digitizes the signals and then provides a signal to processor 39. Processor 39, responsive to those signals, provides control signals on line 70 and 72 to the heater elements 17a and 60. If the temperatures are within a predetermined range, then the set point circuit 30 does not adjust the temperatures of the heater element 17a or the heater 60. However, if the temperature of either the heater element 17a or the heater 60 is outside the range, then an adjustment is made through processor 39. After the set point is established, then the gas to be analyzed is provided to the sample cell 13.

Processor 39 is typically a microprocessor that controls various functions of the gas analyzer 10. A typical microprocessor that is utilized in the gas analyzer 10 is model number 68HC11, which is manufactured by Motorola. The processor 39 will process the gas data (i.e., per cent constituent gas in the mixture), while also controlling the stepper motor 25, source 17 and filter heater 60.

Filters 26-1 through 26-3 ($F_1$–$F_3$) filter energy from sample cell 13 and provide that energy to the detectors 27-1 through 27-3 ($D_1$–$D_3$) with appropriate gas signals. Detectors 27-1 through 27-3 ($D_1$–$D_3$) receive the filtered energy from filters 26-1 through 26-3 respectively and produce signal outputs representative thereof. Typically detectors include an amplifier to bring the signal outputs to the appropriate level. The signals from detectors 27-1 through 27-3 are provided to an array 40 of gas channels 40-1 through 40-3.

The gas channels 40-1 through 40-3 are typically A/D converters which convert the AC signals from the detectors 27-1 through 27-3 to DC signals which are representative of the concentration levels of the gases being measured. Gas channels 40-1 through 40-3 provide signals to processor 39. Processor 39 provides an output signal representative of the concentration levels of the gases being measured.

The analyzer 10 operates in the following manner. A gas mixture, typically from an automobile engine exhaust, enters the gas analyzer 10 through valve 14 and then is pumped by pump 20 to the sample cell 13. Source 17 under control of processor 39 directs infrared radiation produced by heater element 17a through sample cell 13 and the infrared radiation is periodically interrupted by the chopper wheel or blade 19 at a predetermined frequency. Source heater element 17a typically comprises a ceramic heater element that generates infrared energy through resistive heating.

The chopper blade 19 is under control of processor 39 via stepper motor 25. Through the use of the stepper motor 25, the chopper blade 19 is rotated through discrete steps which provide for a sharp square wave AC signal output. The dwell time of the chopper blade 19 at each position is selected to provide a desired wave shape. Thus, the chopper blade 19 provides an AC signal which, as is shown in the art, has the effect of canceling out any background DC radiation. In a preferred embodiment, the chopper blade 19 comprises a wedged shaped metal blade encompassing 90° of a circle. The chopper blade 19 is rotated through a 90° excursion in such a manner so as to alternately block the infrared energy passing through sample cell 13. Thus, an AC signal is created at the output of sample cell 13. Of course, one ordinarily skilled in the art will recognize that other types of chopper blade configurations can be utilized to provide the same duty cycle.

In the illustrative embodiment of the present invention, detection signals are produced by the cooperation of filters 26-1, 26-2, 26-3 with detectors 27-1, 27-2, 27-3 corresponding to the infrared radiation received at a preselected wavelength of the gas within sample cell 13. Filters 26-1 through 26-3 and detectors 27-1 through 27-3 are preferably an individual assembly 24 in which an optical filter and a thermopile detector are utilized for each gas to be measured. The assembly 24 includes a resistive heating element 60 to maintain the assembly 24 at a predetermined temperature and thereby eliminate drift corrections required when there are changes in the ambient environment.

The selection of the wavelengths of the respective gases to be detected are determined by respective narrow passband bandpass filters 26-1, 26-2 and 26-3. The source 17 produces the infrared energy that is filtered by filters 26-1 through 26-3. The filtered energy is then received by detectors 27-1 through 27-3, respectively. The AC signal outputs of the detectors 27-1, 27-2 and 27-3, are processed by gas channels 40-1, 40-2 and 40-3, respectively to produce suitable signals and controls for analog to digital conversion by processor 39. These converted signals are systematically related to the concentration of the gas to be detected.

Accordingly, each AC signal produced by the detectors is amplified by amplifiers 29-1, 29-2, 29-3, ($A_1$–$A_3$) integrated by integrators 31-1, 31-2 and 31-3 ($I_1$–$I_3$) and converted to digital format by processor 39 working in conjunction with control logic 33-1, 33-2 and 33-3 ($C_1$–$C_3$). The digital words thus created are systematically related to the concentration of the three gases to be measured in the sample cell 13 (in this example $CO_2$, CO and HC).

The preferred embodiment of the present invention is utilized for detecting the relative presence of gases in the exhaust gas of an automobile engine. The gases of particular interest are hydrocarbons and carbon monoxide. It is recognized, however, by one having ordinary skill in the art that the invention is not limited to use in connection with such specific gases nor is it limited to use in connection with the exhaust gas of an automobile engine. Accordingly, there will be many other uses, apparent to those skilled in the art, for the gas analyzer of the present invention.

It is known that, in prior art gas analyzers, temperature variations in the source as well as in the filter detector assembly affect the accuracy of the analyzer. In particular, it has been found that the detector for each gas channel is temperature sensitive. Accordingly, variations in ambient temperature of the analyzer may cause variations in the output from the detector which will provide an inaccurate indication of each preselected gas in the sample cell.

As before mentioned, Passaro, in U.S. Pat. No. 4,398,091, teaches adjusting the temperatures of the source 17 and heater 60 of the filter/detector assembly 24 so as to ensure that they remain at a desired temperature. Hence, it is known to utilize a differential amplifier circuit to provide the output signal that represents the set point of the gas analyzer.

In the gas analyzer 10, of FIG. 1, the set point circuit 30 receives signals from the source 17 and the heater 60 of the filter/detector assembly 24 representative of the temperatures of those respective elements. As is well known, for accurate measurement of the constituent gases, these temperatures must remain within a predetermined range. It is also very important for the overall accuracy of the gas analyzers that a particular temperature reading from one of the heaters always provide the same output reading to the processor. Hence, the set point circuit 30 is provided to ensure that these temperatures remain constant.

Accordingly, the set point circuit 30 receives a signal representing the temperature of the source 21 and also receives a signal representing the temperature of the filter/detector heater from sensors 150 and 152. The set point circuit 30 then provides output signals representative thereof to processor 39 via analog to digital converter (A/D) 35 through lines 160 and 162.

If one of these signals does not correspond to a reference signal within the set point circuit 30, the processor 39 sends signals on line 90 that will adjust either the temperature of heater element 17a or the heater 60 via lines 70 and 72 such that the signal does match the reference signal. In so doing, a set point is provided that will allow for the subsequent accurate measurement of the constituent gases.

Gas analyzers have typically utilized differential amplifiers for the set point circuit 30. The amplifiers compared the signal produced by the temperature sensors to a reference signal produced within the circuit 30. Although these circuits have worked effectively for their intended purposes, they oftentimes add significant expense to the overall cost of the gas analyzer.

Figures 2, 3:
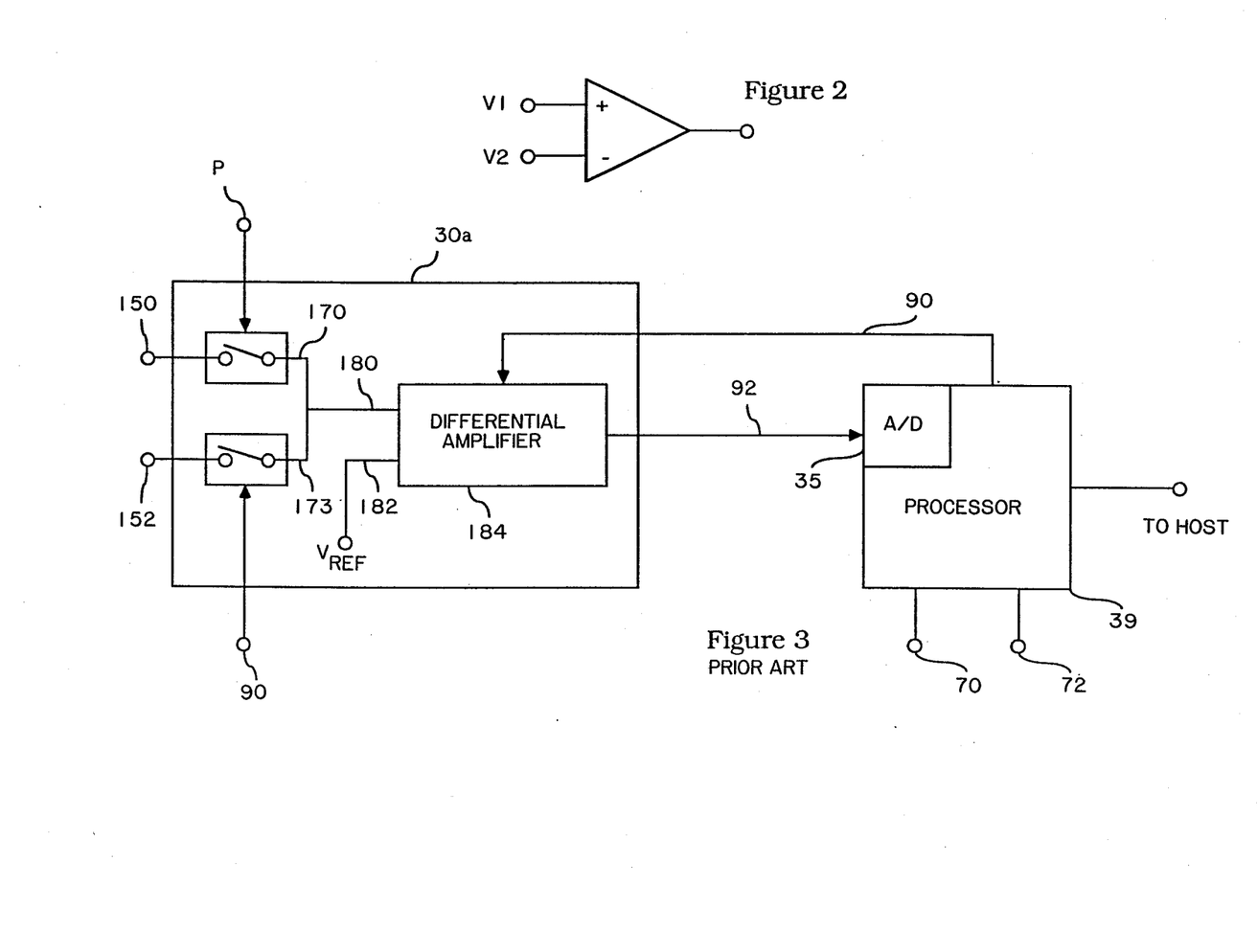
FIG. 2 is a block diagram of a differential amplifier.
FIG. 3 is a block diagram of a prior art set point control circuit utilized in a ga analyzer.

To better explain the difficulties associated with prior art set point circuits, refer now to FIG. 2. FIG. 2 is a block diagram of a differential amplifier 100. As is well known, a differential amplifier is a circuit which amplifies the difference between two input signals. In an ideal differential amplifier the output signal is given by the following equation:

$$V_0 = A_d(V_1 - V_2),$$

where $A_d$ is the gain of the differential amplifier.

Thus, it is seen that if $V_1$ and $V_2$ are equal, the differential output voltage ($V_0$) will be some nominal value. However, a practical differential amplifier is not described by the above equation because, in general, the output signal not only depends upon the difference signal $V_d$ of the two signals but also upon the average level signal, referred to as the common mode signal $V_c$. Accordingly, under certain circumstances, a signal on the output of the amplifier is much greater than the nominal voltage output ($V_o$) even though the input signals ($V_1$ and $V_2$) are equal due to a so-called common mode error. As has been before mentioned, the common mode error is created when the potentials of the input signals are varied together and an output voltage other than nominal is provided.

It is very important that the resistances associated with the differential amplifier be properly matched to ensure that the common mode signal is negligible. Present integrated circuit technology allows for the use of matched resistances in such a configuration; however, these resistances generally must be so-called precision type resistors.

It is well known that precision resistors are significantly more expensive than standard resistors. More particularly, these resistors add significant additional expense to gas analyzers. Since it is very important that the overall cost of the gas analyzer be reduced, any improvement that will eliminate precision resistors will enhance the commercial viability of the gas analyzer. What is meant by precision resistors, in the context of this application, are resistors that are accurate within 10 ppM/° C. and below.

Referring now to FIG. 3, what is shown is a block diagram of a simplified prior art set point circuit 30a, which can be utilized in gas analyzer 10 of FIG. 1. In this embodiment, switches 170 or 172 are activated by appropriate signals from the processor via line 90. Upon activation, the signal from each sensor is compared to $V_{REF}$. The input resistances (not shown) at the inputs 180 and 182 of the amplifier 184 should be precise to ensure that no common mode error is present. Integrated circuit technology allows for the matching of these resistances. However, as before mentioned, if the resistances are matched, the cost of the set point circuit 30a is significantly increased.

In this embodiment, the comparison of $V_{REF}$ to one of the sensors 150 or 152 by differential amplifier 184 provides a DC output signal to the A/D converter 35 which is representative of the difference of these signals. The A/D converter 35 in turn digitizes the signal so as to provide a digital signal to processor 39 that is representative of the difference. If that difference is not within an acceptable range, then the processor 39 sends a signal via line 70 or 72 to adjust the heater associated with the particular sensor 150 or 152. It is very important that the circuit 30a is stable over a range of voltages to ensure that the proper adjustment is made to the source 17 or heater 60.

If there is a common mode error signal provided at the output of the set point circuit 30a, then the processor 39 will adjust the source 17 or heater 60 in response thereto via line 70 or 72. Accordingly, this adjustment would cause an inaccuracy in the subsequent measurement of the constituent gases by the gas analyzer 10. Hence, the stability of set point circuit 30a must be significantly greater than the stability of the reference signal ($V_{REF}$) for proper set point adjustment.

Figure 4:
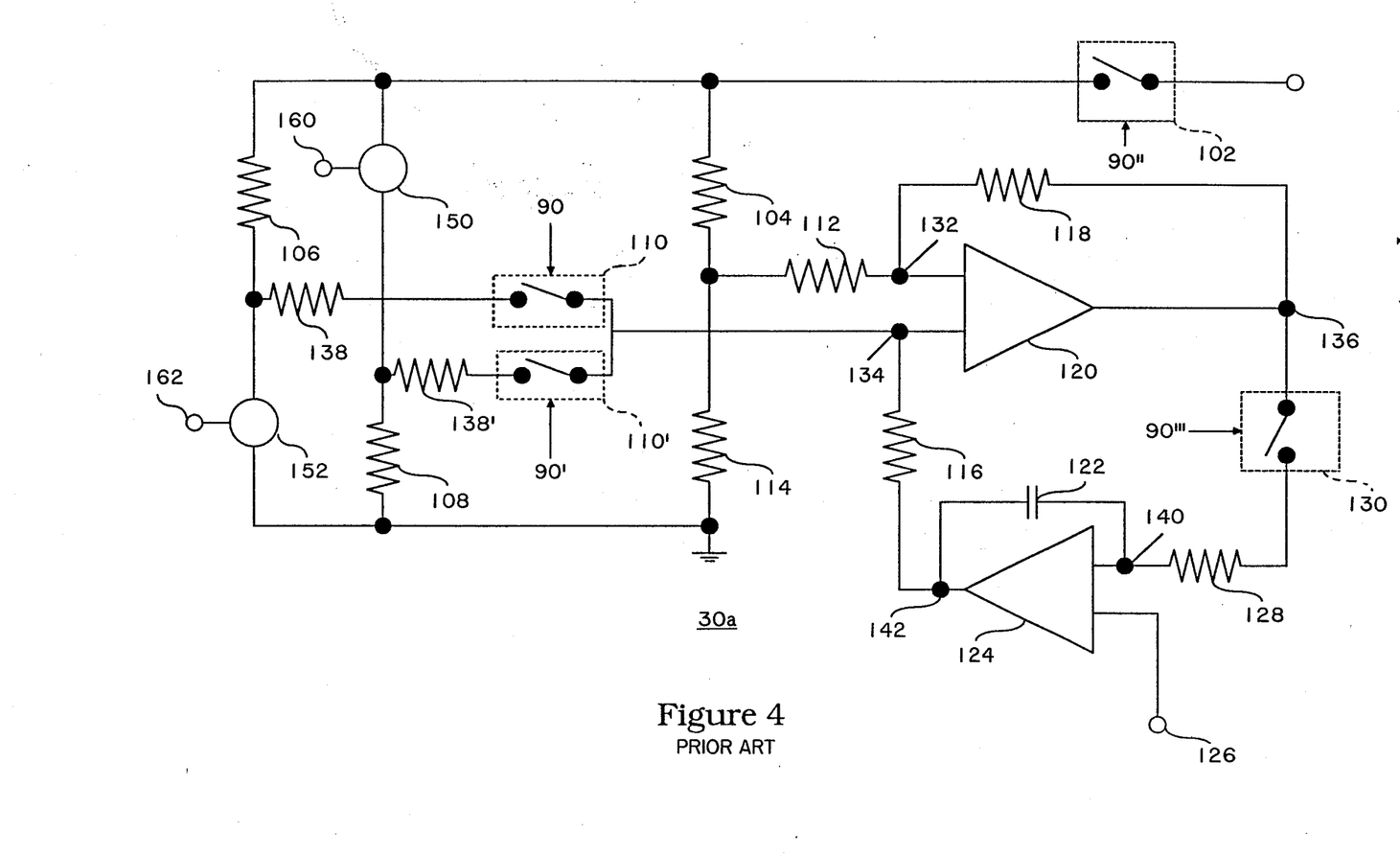
FIG. 4 is a circuit schematic of a prior art set point control circuit.

To more clearly explain this problem, refer now to FIG. 4, which is a circuit diagram of a practical implementation of a prior art set point circuit 30a that is utilized in the gas analyzer 10 of FIG. 1. The set point circuit 30a of FIG. 4 monitors the signals from the source 17 (FIG. 1) and the heating element 60 of the filter/detector unit 24 via sensors 150 and 152, respectively. The set point circuit 30a includes a switch 102, one end of which is coupled to a voltage supply ($V_s$) and the other end of which is coupled in series with one end of resistor 104, one end of sensor 150 and one end of resistor 106. The supply voltage in this embodiment is typically 5 volts to allow for the proper voltage to appear on the output of circuit 30a. Switch 102 is opened and closed by signals from processor 39 via line 90″.

The other end of resistor 106 is coupled to resistor 138 and sensor 152. The other end of sensor 150 is coupled to one end of resistor 108. The other end of resistor 108 is coupled to ground. The resistors 138 and 138′ are also coupled to one end of switches 110 and 110′, respectively. The other ends of switches 110 and 110′ are coupled together and are in turn coupled to the non-inverting input 134 of operational amplifier (OP AMP) 120. The switches 110 and 110′ are opened and closed by appropriate signals from processor 39 via line 90 and 90′.

Resistor 114 is coupled to ground at one end and coupled to resistor 112 at the other. Resistor 112 is coupled to the inverting input 132 of OP AMP 120. Resistor 118 is coupled in feedback relationship with OP AMP 120 between input 132 and output 136. The output 136 of OP AMP 120 is coupled to one end of switch 130. The other end of switch 130 is coupled to a resistor 128. Switch 130 is opened and closed by appropriate signals from processor 39 via line 90‴.

Resistor 128 is in turn coupled to the inverting input 140 of operational amplifier (OP AMP) 124. A reference voltage ($V_{REF}$) is provided at the non-inverting input 126 of OP AMP 124. In a gas analyzer, $V_{REF}$ is typically 2.5 volts and provides a stable voltage that is precise within 0.4%.

A capacitor 122 is coupled in feedback relationship with OP AMP 124 between the input 140 and output 142. The output 142 of OP AMP 124 is coupled to one end of resistor 116. The other end of resistor 116 is coupled to the input 134 of OP AMP 120.

Switches 102, 110, 110′ and 130 can be of a variety of types. In a typical gas analyzer, these switches are field effect transistors (FET's). These switches operate under control of the processor 39 to provide for the different modes of operation of the circuit 30a via line 90, 90', 90'' and 90'''.

The set point circuit 30a has two modes, the calibrating mode and the operating mode. In the calibrating mode, switch 130 is closed and switch 102 and switch 110' are open. In so doing, a closed loop is established whose significant error point is the output 136 of OP AMP 120. The two inputs 132 and 134 of OP AMP 120 are grounded at this point.

The signal at the output 136 of OP AMP 120 feeds through resistor 128 to change the voltage across the capacitor 128 until the current through the resistor ceases. The OP AMP 124 with its feedback connected capacitor operates as an integrator which eliminates the offset voltage of the operational amplifier 120. Hence, the output of the operational amplifier will eventually reach some nominal voltage through this calibration step. This output voltage is delivered to the A/D converter 35 (FIG. 1). The digitized signal is then presented to processor 39. This digitized signal represents the nominal voltage (typically 2.5 volts).

In the operating mode, switch 130 is open and switch 102 is closed and switch 110 is closed and 110' is open. The supply voltage $V_S$ is provided to a bridge network consisting of resistor 106, the sensor 152 in conjunction with the resistance network 104 and 136. The offset voltage that is applied through 118 is maintained at a constant voltage by the capacitor 122. Therefore, the output of the OP AMP 120 is a measure of the variation between the combination of resistors 104 and 114 and the combination of the resistor 106 and the sensor 152.

If the nominal voltage is present on the output of the OP AMP 120, then normal operation of the gas analyzer 10 (FIG. 1) is presumed. If, however, some other voltage is present on the output of OP AMP 120, then the processor will adjust the heater associated with sensor 152 until that nominal voltage is obtained. This operating process can be repeated for the measurement of the other sensor 150 by activation of switch 110' and deactivation of switch 110.

Although the circuit 30a operates effectively for its intended purpose, the problem with this arrangement is that there is a common mode error that is not cancelled at the reference level. What is meant by that is that all the resistors interact with the ability of the circuit 30a to measure the exact value of deviation from the set point. Hence, although the sensor voltage may not vary from the reference voltage, these resistances, if not precise, can cause an erroneous voltage to be present on the output of the circuit 30a. Therefore, an inaccurate signal will be provided to the processor 39. Hence, the processor 39 will adjust the associated heater, thereby adversely affecting the accuracy of the gas analyzer.

In particular, the ratios of the switch 110 resistance together with resistance 138, resistance 106 and resistance 152 and the ratios of resistance 112 together with resistance 104 and 136 must match to ensure that the set point adjustment is accurate. Hence, all of these resistors must be precision resistors. In addition, the offset current through resistor 116 will often produce different offset currents through resistors 138' and 138, thereby requiring that they also be precision resistors.

These considerations require that the abovementioned resistors must be considerably more stable than set point stability requirements. Precision resistors are significantly more expensive than standard resistors. For example, a typical precision resistor utilized in the set point circuit 30a would cost approximately $7.00, whereas a standard resistor would cost approximately $0.04.

Hence, precision resistors add an expense that prohibitively affects the commerciality and feasibility of the circuit 30a's use in a gas analyzer. As the need arises for less expensive and more reliable gas analyzers, there is a corresponding need to reduce the various component parts of the gas analyzer wherever possible.

Hence, although the set point circuit 30a works effectively for its intended purpose, what is needed is a set point control circuit for gas analyzers which overcomes the above-mentioned deficiencies.

Figure 5:
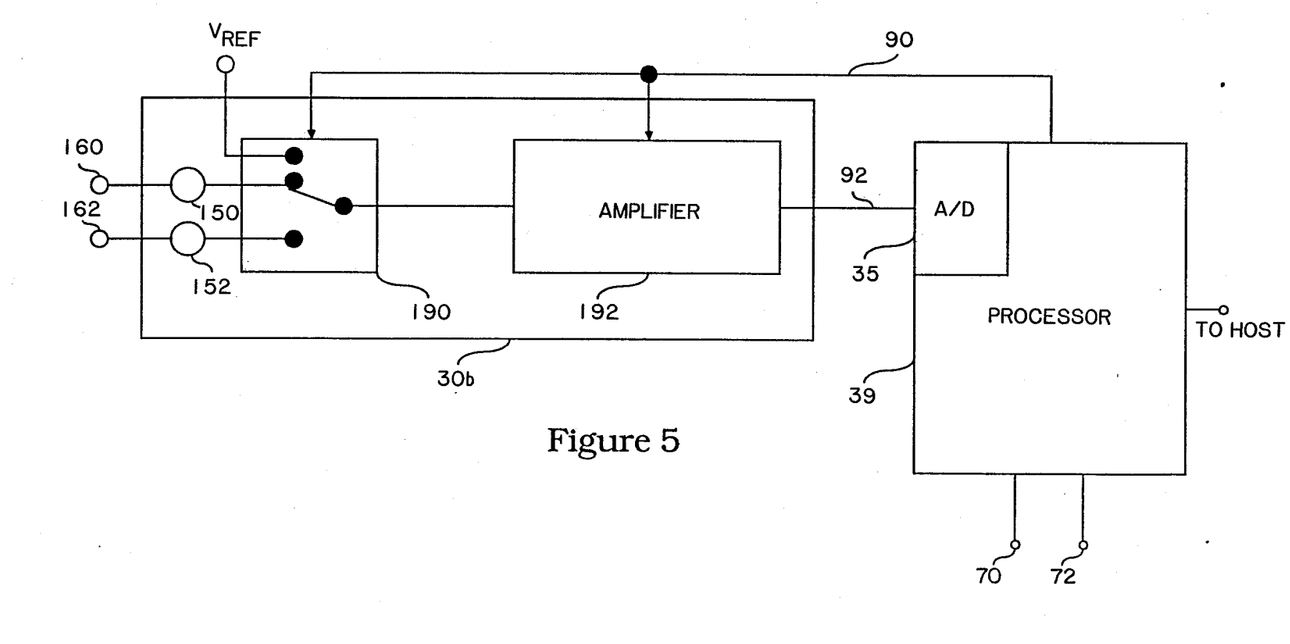
FIG. 5 is a block diagram of a set point control circuit in accordance with the present invention.

Refer now to FIG. 5, which is a block diagram of a stable set point control circuit 30b in accordance with the present invention. What is shown is an amplifier 192, which is coupled to first a reference voltage input and then selectively switched by switch 190 to either the sensor 150 or the sensor 152 through operation of processor 39. Through the selective switching of the amplifier 192 between one of the sensor inputs and the reference input by processor 39, the measurement of the signals becomes a time-based measurement rather than a direct comparison measurement as shown in the above prior art circuit 30a. In so doing, the set point circuit 30b becomes a much less expensive portion of the gas analyzer 10.

The present invention provides for $V_{REF}$ to be converted by the A/D converter 35. The A/D converter 35 provides a first DC signal to the processor 39, representative of the reference input. Thereafter, the amplifier is switched to one of the sensors (150 or 152) and is thereafter presented to the A/D converter 35. A second DC signal is then presented to the processor 39 that is representative of that sensor signal. The first and second DC signals representing the sensor input and reference signal are compared within the processor 39. If there is a difference between the two signals, the processor 39, via line 70 or 72, adjusts the heater associated with that sensor (150 or 152) to bring the sensor signal into correspondence with $V_{REF}$.

Through this arrangement, the magnitude of the difference between the sensor signal and the reference signal is rendered relatively insensitive to control performance, i.e., a 10% misestimation of error will not affect final set point accuracies, unlike the prior art arrangement of FIGS. 3 and 4. The important feature is that the amplifier 192 present equivalent outputs to the processor 39 when the amplifier is switched between the $V_{REF}$ and a sensor by switch 190. Accordingly, the processor 39 in response to a comparison therewithin will thereafter adjust the heater associated with that sensor until the output signal provided to processor 39 is the same as the output signal provided by $V_{REF}$ when it is coupled to amplifier 192. Hence, since the exact gain of the respective error signals is unimportant, then precision resistors are not needed in the amplifier 192. This elimination of precision resistors represents a significant reduction in the cost of the set point circuit 30b as well as reducing the overall cost of the gas analyzer 10.

Figure 6:
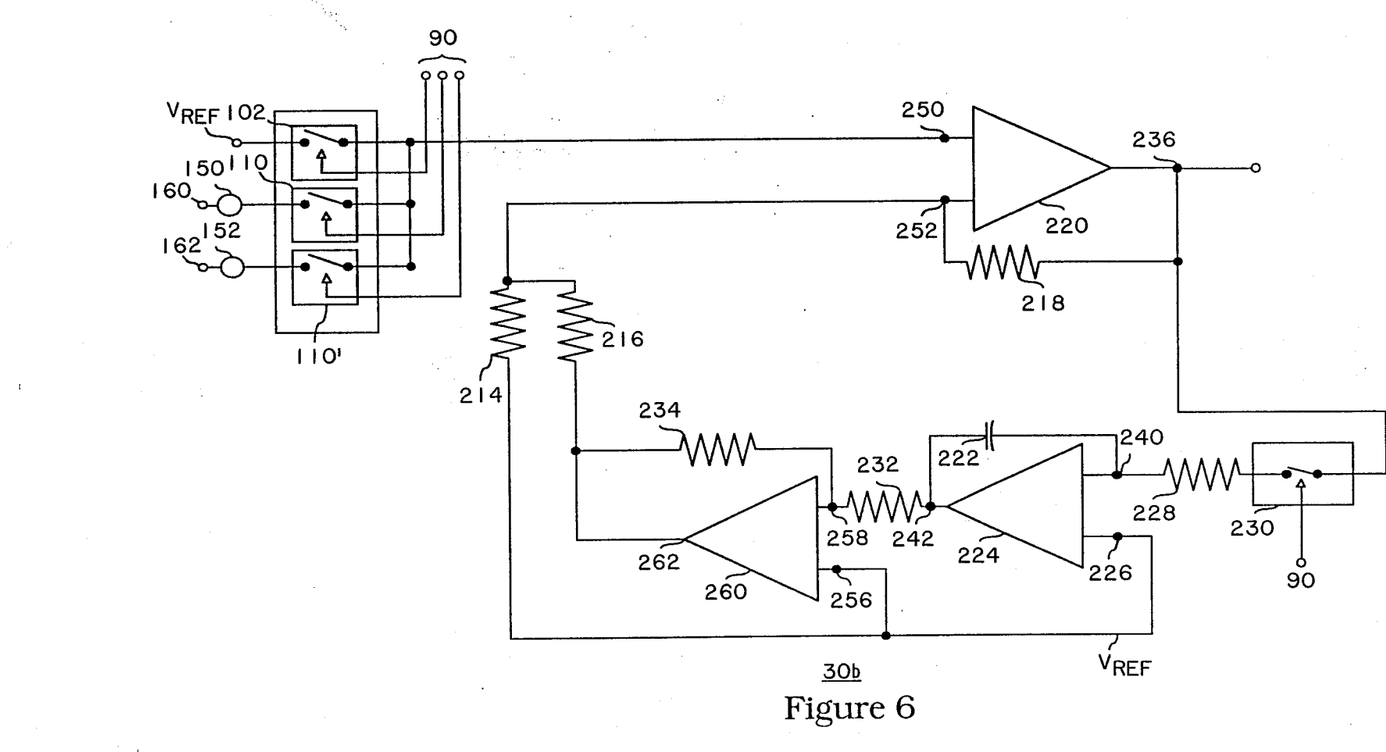
FIG. 6 is a circuit schematic diagram of the set point control circuit in accordance with the present invention.

To more fully explain the present invention, refer now to FIG. 6, which is a circuit diagram of an embodiment of the set point circuit 30b of the present invention. The set point circuit 30b comprises switch 110 and 110' which, similar to the circuit of FIG. 3, connect the sensors 150 and 152, respectively, to the remaining portions of the circuit. Switch 110 is coupled to the non-inverting input 250 of an operational amplifier (OP AMP) 220. The inverting input 252 of OP AMP 220 is coupled in feedback relationship with a resistor 218 and is also coupled to resistors 214 and 216. The output 236 of OP AMP 220 is coupled to a switch 230. The switch 230 is coupled to a resistor 228, which in turn is coupled to the inverting input 240 of an operational amplifier (OP AMP) 224.

A capacitor 222 is coupled in feedback relationship with OP AMP 224 between inverting input 240 and output 242. The non-inverting input 226 of OP AMP 224 is coupled to a reference voltage ($V_{REF}$) and also coupled to the non-inverting input 256 of an operational amplifier 260. As described with reference to FIG. 4, $V_{REF}$ can be a stable voltage of 2.5 volts which is precise to 0.4%. $V_{REF}$ is coupled to the other end of resistor 214. Coupled to the output 242 of OP AMP 224 is a resistor 232, which in turn is coupled to the inverting input 258 of the operational amplifier (OP AMP) 260. A resistor 234 is coupled in feedback relationship with OP AMP 260 between input 258 and output 262. The output 262 of OP AMP 260 is coupled to one end of resistor 216.

This circuit 30b monitors the control sensors 150 and 152 and adjusts the heaters in accordance with the respective input signals. An amplifier circuit comprising OP AMPs 220, 224 and 260 and the resistors 214, 216, 218, 234, 232 and 228 and the capacitor 222 represents the amplifier 192 of FIG. 5. The processor 39 eliminates through control lines 70 and 72 the difference between the signals produced by either of the sensors 150 and 152 and the reference voltage $V_{REF}$.

The present invention operates in the following manner. In the calibrating mode, the switches 110 and 110' are open and switch 102 is closed and switch 230 is closed. Accordingly, a closed loop is established whose significant error point is the output of OP AMP 220. The signal feeds through resistor 228 to change the voltage across capacitor 222 until the current ceases. At this time, the output of OP AMP 220 is equal to the reference voltage $V_{REF}'$ provided at OP AMP 224 minus an offset voltage. The output is read at the output 236 of OP AMP 220 and this value is established as the set point.

In the operating mode, switch 230 is open and switch 102 is open. Then switch 110 is closed. Accordingly, the output of sensor 150 is compared to the voltage received when switch 102 is closed, which, in this embodiment, is the reference ($V_{REF}$). Therefore, the variation of the voltage of the sensor 150 can be compared to the reference voltage, in time, by switching the control circuit 30a between switches 110 and 102. Similarly, the variations between the sensor 152 and the reference voltage can be compared in time by switching the control circuit 30b between switches 110' and 102.

In this embodiment, the exact scale factor of the variation is relatively unimportant and therefore all of the resistances utilized can be standard resistors. Since both signals (reference and sensor) are being provided through the amplifier circuit, their outputs can be compared by processor 39. Hence, the value or magnitude of the output signal is not important. What is important is that the reference signal and the sensor signal correspond to each other and that $V_{REF}$ is a stable voltage.

By switching the amplifier circuit between the sensors and the reference and then comparing the signals within the processor 39, the set point circuit 30b is significantly less expensive than the prior art circuit 30a of FIG. 4. Through the use of this set point circuit 30b in conjunction with the processor 39, no precision resistors are necessary, thereby providing a gas analyzer which is less expensive than those previously known.

While a preferred embodiment of the invention has been illustrated, it will be obvious to one of ordinary skill in the art that various modifications and changes may be made thereto without departing from the spirit and scope of the present invention.

Specifically, the processor described in the present invention can be a variety of other types of devices. More particularly, discrete logic circuitry could be utilized to perform the switching of the control set point control circuit between the reference voltage and the sensors. Also, many types of stable reference voltage generators are known and could be utilized in accordance with the present invention.

Further, it is known that although there are two sensors utilized in the illustrative embodiments of the present invention, there could be any number of sensors utilized. Finally, although temperature is the parameter utilized to provide the set point embodiment, other parameters such as pressure, humidity or the like could be utilized to provide a set point for the gas analyzer.

Accordingly, while this invention has been described by means of a specific illustrative embodiment, the principles thereof are capable of a wide range of modification by one skilled in the art. Hence, the present invention is limited only by the scope of the following claims.

What is claimed is:

1. A circuit for providing a stable set point for a gas analyzer comprising:
    means for generating a reference signal;
    a sensor for generating a sense signal, said sense signal being dependent on a parameter of said gas analyzer;
    a set point circuit comprising:
    switch means, having an input and an output, for switching between said reference signal generating means and said sensor; and
    processor means coupled to said output of said switch means for selectively controlling said switch means to alternately couple said input of said switch means between said reference signal generating means and said sensor, and for receiving said signals, said processor means also comparing said reference signal and said sense signal, wherein said processor means is responsive to the comparisons of said reference signal and said sense signal and controls said parameter until said sense signal corresponds to said reference signal to provide the stable set point for said gas analyzer.

2. The circuit of claim 1 in which said switch means further includes:
    an amplifier having an input and output, said input of said amplifier being switchable to be selectively coupled to said reference signal generating means and to said sensor for providing a signal representative of said reference signal on said output when coupled thereto and providing a signal representative of said sensor on said output when coupled thereto.

3. The circuit of claim 2 which further comprises:
    means coupled to said amplifier for converting said reference signal and said sense signal to first and second digital signals; wherein said processor means compares said first and said second digital signals and controls said parameter until said second digital signal corresponds to said first digital signal.

4. The circuit of claim 3 wherein said set point circuit further comprises:
a first switch coupled to said sensor;
a first operational amplifier having inverting and noninverting inputs and an output; said non-inverting input of said first operational amplifier coupled to said first switch;
a second switch coupled to said output of said first operational amplifier;
an integrator with first and second inputs and an output for eliminating an offset voltage provided by said first operational amplifier; said first input of said integrator coupled to said second switch; said second input of said integrator coupled to said reference voltage generating means; and
a second operational amplifier having an inverting and a non-inverting input and an output; said inverting input of said second amplifier coupled to said output of said integrator; said inverting input of said second amplifier coupled to said reference voltage generating means; said output of said second amplifier coupled to said inverting input of said first amplifier.

5. The circuit of claim 4 wherein said first operational amplifier further comprises a first resistor coupled in a feedback relationship between said inverting input and said output of said first amplifier.

6. The circuit of claim 5 wherein said second operational amplifier further comprises a resistor coupled in feedback relationship between said inverting input and said output of said second amplifier.

7. The circuit of claim 6 wherein said integrator comprises a third operational amplifier with an inverting and a non-inverting input and an output; and a capacitor coupled between said inverting input and said output of said third operational amplifier.

8. The circuit of claim 7 which further comprises a resistor coupled between said second switch and said inverting input of said integrator.

9. The circuit of claim 8 which further comprises a resistor coupled between said output of said integrator and said inverting input of said second operational amplifier.

10. The circuit of claim 9 which further comprises a resistor coupled between said non-inverting input of said second operational amplifier and said inverting input of said first operational amplifier.

11. The circuit of claim 10 wherein each of said first and second switches comprises a field effect transistor.

12. The circuit of claim 11 wherein said processor means comprises a microprocessor.

13. The circuit of claim 12 wherein said parameter is temperature.

14. The circuit of claim 13 wherein said converting means comprises an analog to digital converter.

15. A method for providing a stable set point for a gas analyzer comprising the steps of:
(a) generating a reference signal;
(b) converting said reference signal to a first digital signal;
(c) sending said first digital signal to a processor;
(d) generating a signal that is dependent on a parameter of said gas analyzer;
(e) converting said parameter signal to a second digital signal;
(f) sending said second digital signal to said processor;
(g) comparing said second digital signal to said first digital signal within said processor; and
(h) controlling said parameter in response to said comparing of said first and second digital signals.

16. The method of claim 15 wherein said parameter is temperature.

17. A non-dispersive gas analyzer comprising:
a sample cell for containing a first sample gas mixture to be analyzed for the presence of a predetermined gas;
means for directing infrared energy through said sample cell;
means for modulating the amplitude of said infrared energy;
means for detecting the infrared energy passing through said sample cell at the characteristic wavelength of said predetermined gas and producing an output signal representative thereof;
means for heating said detecting means to a predetermined temperature; and
means responsive to said directing means and said heating means for providing a stable set point for said gas analyzer; wherein said stable set point providing means comprises:
means for generating a reference signal;
a sensor for generating a sense signal; said sense signal being dependent on said predetermined temperature;
a set point circuit comprising:
an amplifier having an input and output, said input of said amplifier being switchable to be selectively coupled to said reference signal generating means and to said sensor, said amplifier providing a signal representative of said reference signal on said output of said amplifier when coupled thereto and providing a signal representative of said sensor on said output of said amplifier when coupled thereto; and
switch means with an input and output, said input of said switch means being switchable to be alternately coupled to said reference signal generating means and said sensor, and said output of said switch means being coupled to said input of said amplifier;
means coupled to said output of said amplifier for converting said reference signal and said sense signal to first and second digital signals; and
processor means for selectively controlling said switch means to alternately couple said input of said amplifier between said reference signal generating means and said sensor to provide said first and second digital signals, said processor means also comparing said first and second digital signals, wherein said processor means responsive to the comparing of said first and second digital signals adjusts said heating means until said second digital signal corresponds to said first digital signal, 18. The gas analyzer of claim 17 wherein said st point circuit further comprises:
a first switch coupled to said sensor;
a first operational amplifier having an inverting and a non-inverting input and an output; said non-inverting input of said first operational amplifier coupled to said first switch;
a second switch coupled to said output of said first operational amplifier;

an integrator with first and second inputs and an output for eliminating an offset voltage provided by said first operational amplifier; said first input of said integrator coupled to said second switch; said second input of said integrator coupled to said reference voltage generating means; and a second operational amplifier having inverting and non-inverting inputs and an output; said inverting input of said second operational amplifier coupled to said output of said integrator; said non-inverting input of said second amplifier coupled to said reference voltage generating means; said output of said second operational amplifier coupled to said inverting input of said first amplifier.

19. The gas analyzer of claim 18 wherein said first operational amplifier further comprises a first resistor coupled in a feedback relationship between said inverting input and said output of said first operational amplifier.

20. The gas analyzer of claim 19 wherein said second operational amplifier further comprises a resistor coupled in feedback relationship between said inverting input and said output of said second operational amplifier.

21. The gas analyzer of claim 20 wherein said integrator comprises a third operational amplifier with an inverting and non-inverting input and an output; and a capacitor coupled between said inverting input and said output of said third operational amplifier.

22. The gas analyzer of claim 21 wherein said stable set point providing means further comprises a resistor coupled between said second switch and said inverting input of said integrator.

23. The gas analyzer of claim 22 in which said stable set point providing means further comprises a resistor coupled between said output of said integrator and said inverting input of said second operational amplifier.

24. The gas analyzer of claim 23 wherein said stable set point providing means further comprises a resistor coupled between said non-inverting input of said second operational amplifier and said inverting input of said first operational amplifier.

25. The gas analyzer of claim 24 wherein said stable set point providing means further comprises a resistor coupled between said output of said second operational amplifier and said non-inverting input of said first operational amplifier.

26. The gas analyzer of claim 25 wherein each of said first and second switches comprises a field effect transistor.

27. The gas analyzer of claim 26 wherein said processor means comprises a microprocessor.

28. The gas analyzer of claim 27 wherein said converting means comprises an analog to digital converter.

* * * * *

UNITED STATES PATENT AND TRADEMARK OFFICE
CERTIFICATE OF CORRECTION

PATENT NO. : 4,918,311
DATED : April 17, 1990
INVENTOR(S) : Raymond E. Rogers

It is certified that error appears in the above-identified patent and that said Letters Patent is hereby corrected as shown below:

Column 4, line 23, delete "ga" and insert therefor --gas--.

Column 14, line 60, delete "st" and insert therefor --set--.

Signed and Sealed this

Second Day of June, 1992

Attest:

DOUGLAS B. COMER

*Attesting Officer*   *Acting Commissioner of Patents and Trademarks*